(12) United States Patent
Lee et al.

(10) Patent No.: US 11,019,998 B2
(45) Date of Patent: Jun. 1, 2021

(54) FUNDUS CAMERA AND METHOD FOR SELF-SHOOTING FUNDUS

(71) Applicant: Medimaging Integrated Solution, Inc., Hsinchu (TW)

(72) Inventors: Yu-Tsung Lee, Hsinchu (TW); Yung-En Kuo, Hsinchu (TW)

(73) Assignee: MEDIMAGING INTEGRATED SOLUTION, INC., Hsinchu (TW)

(*) Notice: Subject to any disclaimer, the term of this patent is extended or adjusted under 35 U.S.C. 154(b) by 237 days.

(21) Appl. No.: 16/212,089

(22) Filed: Dec. 6, 2018

(65) Prior Publication Data
US 2020/0121185 A1    Apr. 23, 2020

(30) Foreign Application Priority Data
Oct. 18, 2018  (TW) .................. 107136636

(51) Int. Cl.
| A61B 3/12 | (2006.01) |
| A61B 3/14 | (2006.01) |
| A61B 3/00 | (2006.01) |
| A61B 3/15 | (2006.01) |
| A61B 3/103 | (2006.01) |

(52) U.S. Cl.
CPC .............. *A61B 3/12* (2013.01); *A61B 3/0091* (2013.01); *A61B 3/103* (2013.01); *A61B 3/14* (2013.01); *A61B 3/152* (2013.01); *A61B 3/0008* (2013.01); *A61B 3/0041* (2013.01); *G06T 2207/30041* (2013.01)

(58) Field of Classification Search
CPC ....... A61B 3/12; A61B 3/0091; A61B 3/0083; A61B 3/103; A61B 3/0008; A61B 3/14
USPC .................................................. 351/246, 206
See application file for complete search history.

(56) References Cited

U.S. PATENT DOCUMENTS

| 3,013,467 | A | * | 12/1961 | Minsky | ............... | G02B 21/002 356/432 |
| 4,023,189 | A | * | 5/1977 | Govignon | .............. | A61B 3/125 396/18 |
| 6,042,232 | A | * | 3/2000 | Luce | ...................... | A61B 3/103 351/212 |
| 7,802,884 | B2 | * | 9/2010 | Feldon | ............... | H04N 5/23206 351/206 |
| 8,696,128 | B2 | * | 4/2014 | Holley | ................. | A61B 5/1455 351/221 |
| 9,532,708 | B2 | * | 1/2017 | Juhasz | ................... | A61B 3/152 |
| 9,895,058 | B2 | * | 2/2018 | Baker | .................... | A61B 3/103 |

(Continued)

FOREIGN PATENT DOCUMENTS

WO    WO-2007082146 A2 *  7/2007 ........... A61B 3/1015

OTHER PUBLICATIONS

Robert H. Webb, George W. Hughes, and Francois C. Delori, "Confocal scanning laser ophthalmoscope," Appl. Opt. 26, 1492-1499 (1987) (Year: 1987).*

*Primary Examiner* — Zachary W Wilkes
(74) *Attorney, Agent, or Firm* — Muncy, Geissler, Olds & Lowe, P.C.

(57) ABSTRACT

A fundus camera displays guide information on a display panel which can be viewed by a testee to guide the testee to adjust a relative position of the fundus camera and a tested eyeball of the testee to a determined position. Therefore, the testee can use the above-mentioned fundus camera to self-shoot fundus images with better image quality. A method for self-shooting fundus is also disclosed.

19 Claims, 5 Drawing Sheets

(56) References Cited

U.S. PATENT DOCUMENTS

| | | | |
|---|---|---|---|
| 9,993,155 B2* | 6/2018 | Cheng | A61B 3/14 |
| 2009/0153796 A1* | 6/2009 | Rabner | A61B 5/14555 |
| | | | 351/201 |
| 2012/0092619 A1* | 4/2012 | Rowe | A61B 3/0016 |
| | | | 351/221 |
| 2019/0125184 A1* | 5/2019 | Kramer | A61B 3/0041 |
| 2019/0254514 A1* | 8/2019 | Westphal | A61B 3/0083 |

* cited by examiner

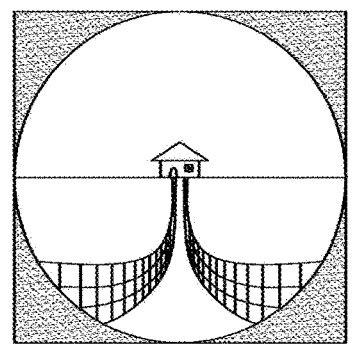
Fig.3
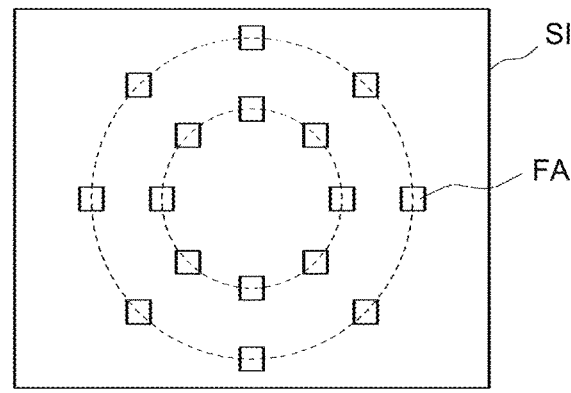
Fig.4
Fig.5

FUNDUS CAMERA AND METHOD FOR SELF-SHOOTING FUNDUS

BACKGROUND OF THE INVENTION

1. Field of the Invention

The present invention relates to a fundus camera and a method for shooting fundus, particularly to a fundus camera the user can operate to self-shoot fundus and a method for self-shooting fundus.

2. Description of the Prior Art

A fundus camera is an instrument for inspecting the fundus of an eyeball, such as for inspecting retinae, optic disc, and vasculature. The conventional fundus cameras are classified into desk-top fundus cameras and handheld fundus camera. In operation of a desk-top fundus camera, the head of a testee is fixed firstly; next, the position of the pupil is acquired by an image recognition technology; then, a servo motor drives the camera to a precise shooting position. The inspector can make the desk-top fundus camera shoot automatically via simple operation. However, the desk-top fundus camera is bulky and inconvenient to carry about. Thus, the application of the desk-top fundus camera is limited.

The conventional handheld fundus camera is powered by batteries, compact, lightweight, convenient to carry about, and thus suitable to shoot fundus in various environments. Constrained by the demands for volume, weight, and battery life, the conventional fundus camera is unsuitable to use a servo motor to acquire a precise shooting position. For a testee with small pupils (e.g. the diameter thereof is less than 3.5 mm), it is difficult to acquire an image of fundus of good quality because the illumination light is hard to illuminate the fundus unless the illumination light is aligned to the pupil precisely. Therefore, the conventional handheld fundus camera must be operated by the inspector to shoot the fundus, not to mention that the testee operates it to self-shoot his own fundus.

Accordingly, a fundus camera that the testee can use to self-shoot his own fundus has been a target the manufacturers desire to achieve.

SUMMARY OF THE INVENTION

A fundus camera and a method for self-shooting fundus are provided herein. Guide information is presented on a display panel visible to the testee to guide the testee adjust a relative position of the fundus camera and the tested eyeball to a predetermination position, whereby the testee can self-shoot his own fundus of better image quality.

Accordingly, the fundus camera includes a first lens group, an illumination element, a second lens group, an image sensor, a light splitter, a third lens group, a first display panel, a processor, and a communication interface. The first lens group has a first side and a second side opposite to the first side. The first side faces a tested eyeball of a testee. The illumination element is disposed on the second side of the first lens group. The first lens group converges the illumination light provided by the illumination element to the tested eyeball. The second lens group is coaxial with the first lens group and disposed on the second side of the first lens group. The image sensor is disposed on a light output side of the second lens group. An imaging light from the tested eyeball is converged by the first lens group and the second lens group to the image sensor to form a sensation image. The light splitter is disposed on the second side of the first lens group, splitting an optical axis of the first lens group into a first sub-optical axis and a second sub-optical axis. The first sub-optical axis is the extension of the optical axis of the first lens group. The third lens group is coaxially disposed on the second sub-optical axis. The first display panel is disposed on a light input side of the third lens group. An image light generated by the first display panel is converged by at least the third lens group, the light splitter, and the first lens group in sequence to the tested eyeball. The processor is electrically connected with the image sensor and the first display panel. The processor presents guide information on the first display panel to guide the testee to adjust a relative position of the fundus camera and the tested eyeball to a predetermination position, whereby the testee can self-shoot his own fundus. The communication interface is electrically connected with the processor, enabling the fundus camera to communicate with an external electronic device.

In another embodiment, the method for self-shooting fundus includes: providing a fundus camera; displaying guide information on a display panel; and the guide information guiding the testee adjust a relative position of the fundus camera and the tested eyeball to a predetermination position for self-shooting fundus, wherein the fundus camera includes a first lens group, an illumination element, a second lens group, an image sensor, a light splitter, a third lens group, and a first display panel, and wherein an illumination light generated by the illumination element is converged by the first lens group to a tested eyeball of a testee, and wherein an imaging light from the tested eyeball is converged by the first lens group and the second lens group to the image sensor and form a sensation image, and wherein an image light generated by the first display panel is converged by at least the third lens group, the light splitter, and the first lens group to the tested eyeball; presenting guide information on the first display panel; and according to the guide information, the testee adjusting a relative position of the tested eyeball and the fundus camera to a predetermined position for photography.

In yet another embodiment, the fundus camera of the present invention includes a first lens group, an illumination element, a second lens group, an image sensor, a second display panel, a processor, and a communication interface. The first lens group has a first side and a second side opposite to the first side. The first side faces a tested eyeball of a testee. The illumination element is disposed on the second side of the first lens group. The first lens group converges the illumination light provided by the illumination element to the tested eyeball. The second lens group is coaxial with the first lens group and disposed on the second side of the first lens group. The image sensor is disposed on a light output side of the second lens group. An imaging light from the tested eyeball is converged by the first lens group and the second lens group to the image sensor to form a sensation image. The second display panel is electrically connected with a processor and presents the sensation image. The processor is electrically connected with the image sensor and the second display panel. Guide information is presented by the processor on the second display panel, viewed by an untested eyeball of the testee and guiding the testee to adjust a relative position of the fundus camera and the tested eyeball to a predetermination position, whereby the testee can self-shoot his own fundus. The communication interface is electrically connected with the processor, enabling the fundus camera to communicate with an external electronic device.

Below, embodiments are described in detail in cooperation with the attached drawings to make easily understood the objectives, technical contents, characteristics and accomplishments of the present invention.

BRIEF DESCRIPTION OF THE DRAWINGS

FIG. 3 is a diagram schematically showing an optometric pattern presented on a first display panel of a fundus camera according to one embodiment of the present invention;

FIG. 4 is a diagram schematically showing focused areas of a sensation image captured by a fundus camera in an optometric process according to one embodiment of the present invention;

FIG. 5 is a diagram showing dioptric information obtained by a fundus camera in an optometric process according to one embodiment of the present invention;

DESCRIPTION OF THE PREFERRED EMBODIMENTS

Figure 1:
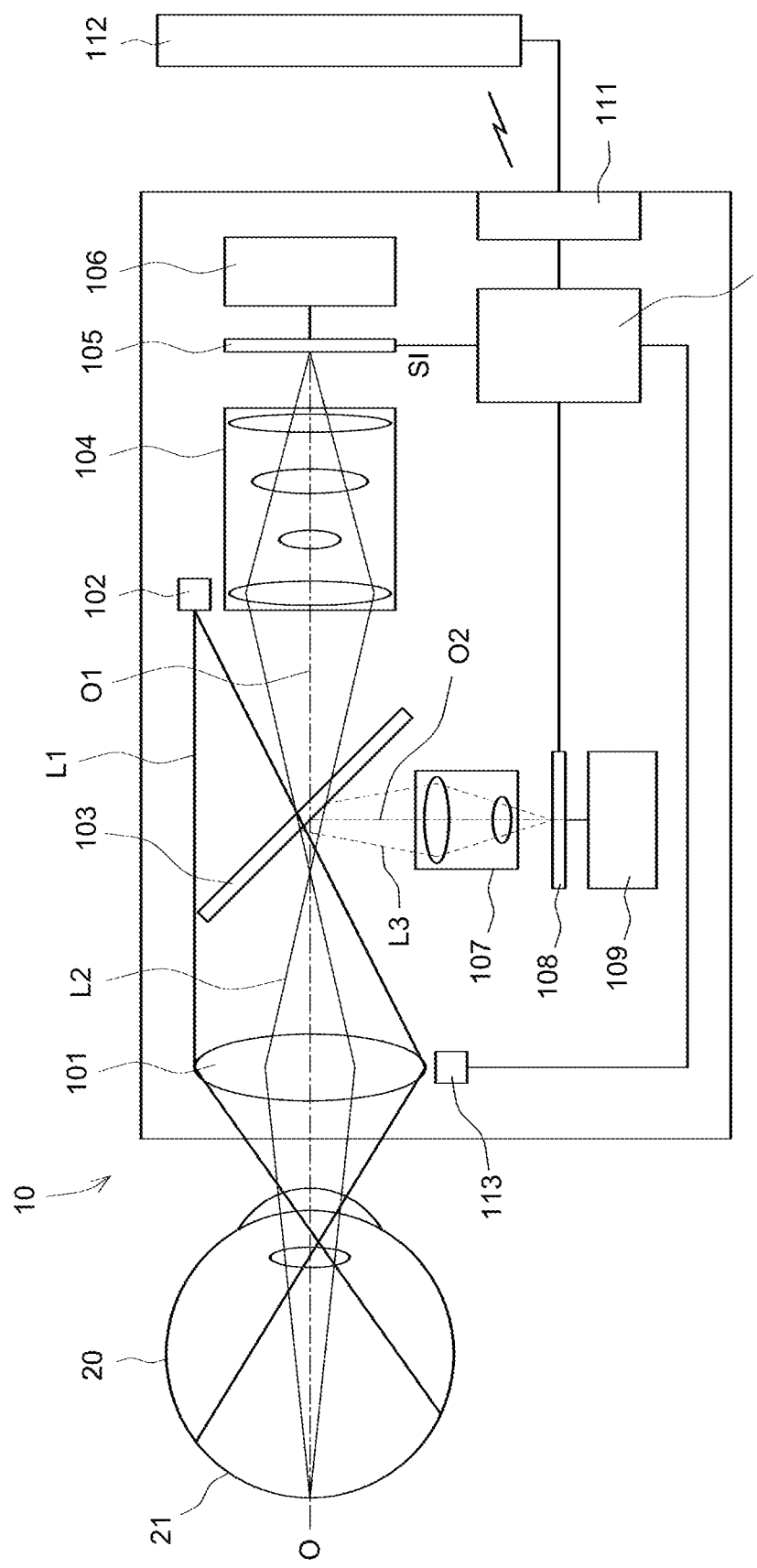
FIG. 1 is a diagram schematically showing a fundus camera according to one embodiment of the present invention.

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in that art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings.

Referring to FIG. 1, an exemplary fundus camera 10 of the present invention includes a first lens group 101, an illumination element 102, a light splitter 103, a second lens group 104, an image sensor 105, a third lens group 107, a first display panel 108, a processor 110, and a communication interface 111. A first side of the first lens group 101 faces a tested eyeball 20 of a testee. A second side of the first lens group 101 is opposite to the first side. The illumination element 102 is disposed on the second side of the first lens group 101. The first lens group 101 converges an illumination light L1 provided by the illumination element 102 to the tested eyeball 20 of the testee. In the embodiment shown in FIG. 1, the illumination element 102 is deviated from an optical axis O of the first lens group 101. However, the present invention is not limited by this embodiment. In some embodiments, the illumination element 102 provides annular illumination. In case of annular illumination, the illumination element providing an annular illumination may be a condenser lens, a light baffle with a ring-shape opening, a relay lens, or a reflective mirror with a circular opening. In one embodiment, the illumination element 102 includes at least a visible light emitting element and at least an infrared light emitting element. In a preferred embodiment, the visible light emitting element and the infrared light emitting element are arranged to form a confocal design. The infrared light emitting element may function as the light source for searching the fundus. The visible light emitting element may function as the light source for photography.

It is understood that according to the principles of optics, the position of the illumination element and the position able to form the smallest light spot satisfy the object-image relationship. Taking the embodiment shown in FIG. 1 in designing an illumination system, a better light utilization efficiency may be achieved by determining an appropriate operating distance between the fundus camera 10 and the tested eyeball 20 to determine the position of the illumination element 102. For example, a better light utilization efficiency is achieved by arranging the illumination element 102 at a position of the object side of the first lens group 101 and determining the smallest light spot at a position of the image side of the first lens group 101 and the pupil at a position of the image side of the first lens group 101.

The second lens group 104 is coaxially disposed on the second side of the first lens group 101. The image sensor 105 is disposed in the light output side of the second lens group 104. In such an architecture, an imaging light L2 from the fundus 21 of the tested eyeball 20 is converged by the first lens group 101 and the second lens group 104 to the image sensor 105 to form a sensation image SI. In one embodiment, the imaging light L2 forms an intermediate image between the first lens group 101 and the second lens group 104 beforehand and then forms an image on the image sensor 105.

The light splitter 103 disposed on the second side of the first lens group 101 splits the optical axis O into a first sub-optical axis O1 and a second sub-optical axis O2. The first sub-optical axis O1 may be viewed as the extension of the optical axis O of the first lens group 101. It is understood that the first sub-optical axis O1 may be regarded as being coaxial with the optical axis O. In the embodiment shown in FIG. 1, the light splitter 103 is disposed between the first lens group 101 and the second lens group 104, but it is not limited to. In one embodiment, the light splitter 103 is disposed between the second lens group 104 and the image sensor 105.

The third lens group 107 is coaxially disposed on the second sub-optical axis O2. The first display panel 108 is disposed on the light input side of the third lens group 107. An image light L3 generated by the first display panel 108 is converged by the third lens group 107, the light splitter 103 and the first lens group 101 to the fundus 21 of the tested eyeball 20, whereby the testee can see the image presented by the first display panel 108.

The processor 110 is electrically connected with the image sensor 105 and the first display panel 108. The processor 110 presents guide information on the first display panel 108. In one embodiment, the processor 110 also presents the sensation image SI output by the image sensor 105 on the first display panel 108. In such an architecture, the testee may adjust a relative position between the fundus camera 10 and the tested eyeball 20 by himself or herself according to the guide information presented by the first display panel 108. While the relative position of the fundus camera 10 and the tested eyeball 20 is at a predetermined position, the captured fundus image has a better quality. The method to guide the testee to adjust the relative position of the fundus camera 10 and the tested eyeball 20 will be explained below. The communication interface 111 is electrically connected with the processor 110 to enable the fundus camera 10 to communicate with an external electronic device. The external electronic device may be a display device, a computer, a mobile Internet access device, or a cloud database. In one embodiment, the communication interface 111 may be a wired communication interface or a wireless communication interface. For example, the communication interface 111 may be a wired USB, a wireless USB (Universal Serial Bus), a Bluetooth device, a WLAN (Wireless Local Area Network), or a mobile communication network.

In one embodiment, the fundus camera of the present invention further includes a first focal length adjuster 106. The fundus of the tested eyeball 20 may be imaged on the image sensor 105 by operating the fundus camera 10 with the first focal length adjuster 106. For example, the first focal length adjuster 106 may use a motor or an appropriate mechanism to drive the image sensor 105 to physically move along the optical axis O and thus modify the focal length. Alternatively, the first focal length adjuster 106 may use a motor or an appropriate mechanism to drive at least one lens of the second lens group 104 to physically move along the optical axis O and thus modify the focal length. In one embodiment, the second lens group 104 includes at least one liquid-state lens; the first focal length adjuster 106 adjusts the curvature of the liquid-state lens of the second lens group 104 and thus modifies the focal length.

In one embodiment, the fundus camera of the present invention further includes a second focal length adjuster 109. The second focal length adjuster 109 adjusts the focal length and makes the image presented by the first display panel 108, such as the guide information and/or the sensation image SI output by the image sensor 105, be imaged on the fundus 21 of the tested eyeball 20. It is understood that the testee just only see a blurred image presented by the first display panel 108 while the optical elements are defocused. Similar to the first focal length adjuster 106, the second focal length adjuster 109 can also physically move the position of the first display panel 108 or at least one lens of the third lens group 107 on the second sub-optical axis O2 to modify the focal length. Alternatively, the second focal length adjuster 109 adjusts the curvature of at least one liquid-state lens of the third lens group 107 to modify the focal length.

In one embodiment, the fundus camera of the present invention further includes a second display panel 112. The second display panel 112 is electrically connected with the processor 111 through the communication interface 111 and presents the sensation image SI output by the image sensor 105. In one embodiment, the second display panel 112 is a touch control panel able to receive control instructions input by the testee. In other words, the testee can operate the fundus camera 10 with the second display panel 112. For example, the testee may select the photographing mode and watch the simplified operating process with the touch control panel. It is understood: the second display panel 112 with a touch control function may be an independent touch control panel or a touch control panel integrated with a computer or an Internet access device (such as a smart phone or a tablet computer). In one embodiment, the second display panel 112 is built in the fundus camera of the present invention. In one embodiment, the second display panel 112 is a flip-flop display panel or an external display device.

In one embodiment, the fundus camera of the present invention further includes a distance sensor 113 disposed at the front end of the fundus camera 10 and faced to the testee. The distance sensor 113 can measure a vertical distance between the fundus camera 10 and the testee and outputs the vertical distance to the processor 110. The vertical distance may be presented on the second display panel 112 in an appropriate way by the processor 110 and be as the guide information to guide the testee to adjust the relative position of the fundus camera 10 and the testee eyeball. For example, the testee is guided to move toward or away from the fundus camera 10. It is noted that: the processor 110 may also estimate the vertical distance between the fundus camera 10 and the testee according to the sensation images SI shown in FIGS. 6a-6d. In other words, the distance sensor 113 maybe omitted in some embodiments.

Figure 2:
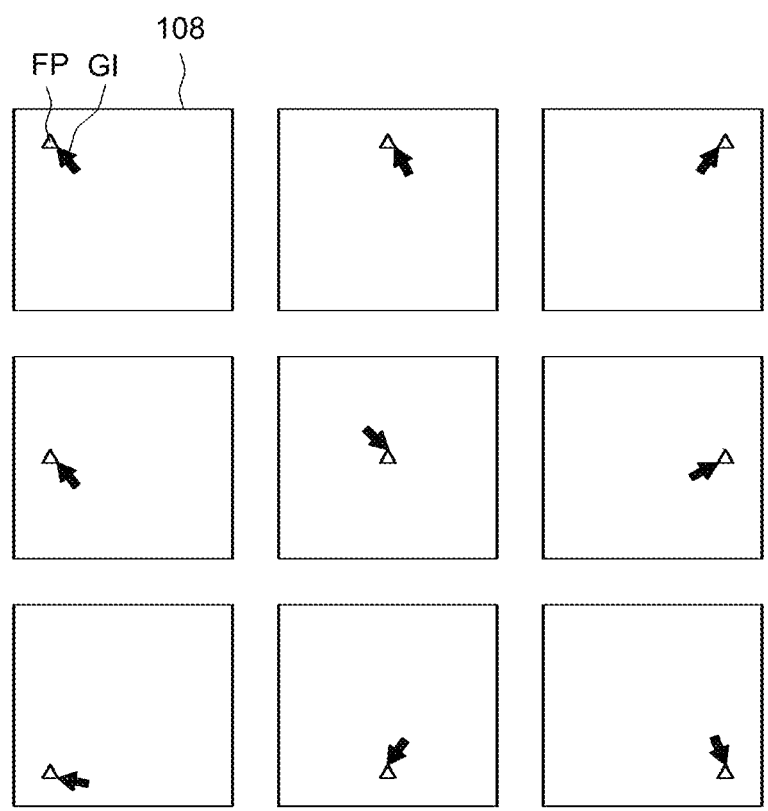
FIG. 2 is a diagram schematically showing fixation patterns and guide information presented on a first display panel of a fundus camera according to one embodiment of the present invention.

Referring to FIG. 2, the processor 110 processes a fixation pattern FP to be presented on the first display panel 108. The fixation pattern FP guides the tested eyeball to rotate to a specific direction, whereby the image sensor 105 can capture the images of different areas of the fundus. For example, the fixation patterns FP shown in FIG. 2 can make the vision line of the testee respectively fixed to the upper left area, upper middle area, upper right area, middle left area, middle area, middle right area, lower left area, lower middle area, and lower right area. In one embodiment, the sensation images, which are respectively captured while the testee eyeball rotates to different directions, are combined to obtain a larger-area fundus image.

It is understood that the testee must fix the rotation angle of the tested eyeball so as to fix the vision line to the fixation pattern FP. As shown in FIG. 2, one of the guide information GI is presented near the fixation pattern FP to prevent the vision line from deflection. In one embodiment, the guide information GI is presented at a fixed position to function as a fixation pattern FP. For example, the fixation patterns FP in FIG. 2 are replaced by the arrow patterns of the guide information GI. In other words, the guide information GI, which is presented as an arrow pattern, is used as the fixation pattern.

The testee may manually adjust the focal length with the second focal length adjuster 109 in order to make the testee see the images presented on the first display panel 108 clearly. In order to simplify the operation of the testee, the processor 110 is electrically connected with the first focal length adjuster 106 and the second focal length adjuster 109 and executes an optometry method to acquire dioptric information of the tested eyeball 20. According to the dioptric information, the processor 110 adjusts the focal length automatically to make the testee view the images presented by the first display panel 108 clearly.

Below is described the optometric process. Firstly, the first display panel 108 presents an optometric pattern shown in FIG. 3. Next, the processor 110 controls the second focal length adjuster 109 to adjust the focal length between the first display panel 108 and the third lens group 107 to induce accommodation relax of the eyeball of the testee. For example, the second focal length adjuster 109 is used to move the first display panel 108 from an equivalent distance of 10 cm to an equivalent distance of infinity. Next, a fogging lens is used to make the testee see the blurred image shown in FIG. 3 and thus relax the eyeball of the testee. While the eyeball of the testee is in accommodation relax, the processor 110 controls the first focal length adjuster 106 to adjust the focal distance between the image sensor 105 and the second lens group 104 and acquire several sensation images. For example, the image sensor 105 may be moved to an equivalent distance of –(m) D (such as –15 D) to capture an infrared sensation image; next, the image sensor 105 may be moved to an equivalent distance of –(m+Δd) D (such as –(15+1) D) to capture an infrared sensation image. The same step is repeated until the image sensor 106 is moved to an equivalent distance of +(n) D (such as +5 D) and captures an infrared sensation image. Thus, totally (m+n)/Δd+1 (such as 21) infrared sensation images are captured. Referring to FIG. 4, the focusing information of the focused area FA of each infrared sensation image SI is analyzed and scored to acquire the one having the highest score to be the diopter of the corresponding focused area. For example, the method of analyzing the focusing information includes steps: obtaining 1-dimensional brightness information of the focused area; undertaking the differentiation of the 1-dimensional brightness information; bisecting the differential; and integrating the bisected differential to acquire the score. Referring to FIG. 5, the optometry result is SPH:–3.0; CYL:–2.0; AXIS:180. SPH means spherical correction, i.e. the required diopters; the minus value is diopters of myopia, and the positive value is the diopters of hyperopia. CYL means cylindrical correction, i.e. the degrees of astigmatism. AXIS is measured in degrees, and refers to the position on the cornea where the astigmatism is located. After the dioptric information of the eyeball 20 is acquired, the processor 110 adjusts the focal length between the first display panel 108 and the third lens group 107 according to the dioptric information, whereby the testee can view the images presented on the first display panel 108 clearly.

Refer to FIGS. 6a-6e for the introduction of how the testee uses the fundus camera of the present invention to self-shoot the fundus images. In FIGS. 6a-6e, the upper drawings schematically show the sensation images SI captured by the image sensor 105; the lower drawings schematically show the fixation patterns FP and the guide information GI presented by the first display panel 108. The fixation pattern FP is presented at the center of the picture. It is understood: the sensation image SI, the fixation pattern FP and the guide information GI may be simultaneously presented on the first display panel 108 to guide the testee to adjust the relative position of the fundus camera 10 and the tested eyeball 20. It should be particularly remarked: the guide information GI shown in FIGS. 6a-6e is presented in form of patterns. For example, the direction of the arrow indicates the direction that the fundus camera 10 or the tested eyeball 20 is moved toward; the length of the arrow indicates the distance of the translation motion along the direction vertical to the optical axis O; the width of the arrow indicates the vertical distance between the fundus camera 10 and the tested eyeball 20. Alternatively, the color of the arrow indicates whether the fundus image appears in the sensation image SI. For example, while the image of a portion of the fundus appears in the field of vision FV of the second lens group 104 in the sensation image SI, the arrow is presented in a specific color, such as the green color; while the image of the fundus does not appear in the field of vision FV, the arrow is presented in another specific color, such as the red color. It is noted: the guide information may be presented in form of other patterns like in various graphical ways, and the guide information GI may also be presented in text to guide the testee.

Figure 6:
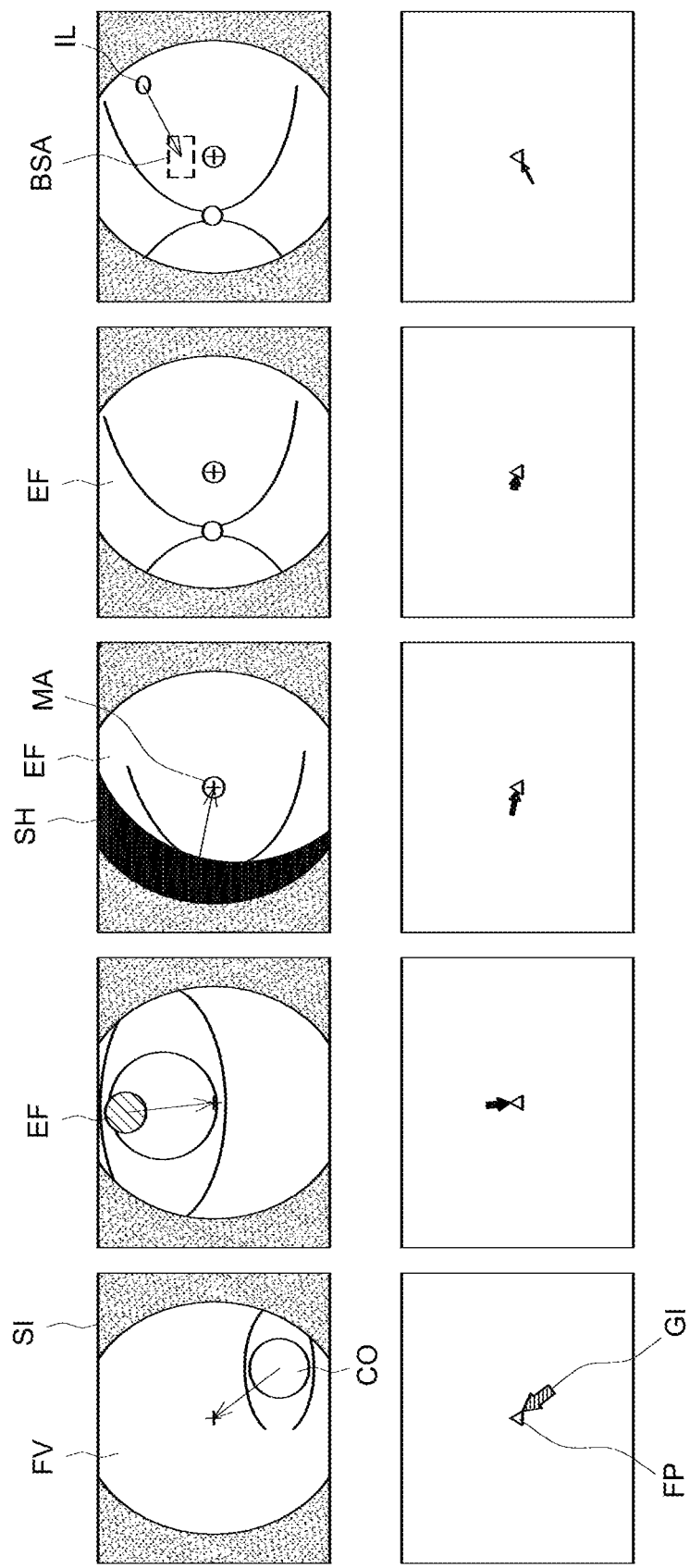
FIGS. 6a-6e are diagrams schematically showing that a fundus camera guides a testee to adjust a relative position of a tested eyeball and the fundus camera according to one embodiment of the present invention.

Referring to FIG. 6a, while the cornea area CO of the tested eyeball 20 appears in the field of vision FV of the sensation image SI, the center of the cornea area CO and the center of the sensation image SI (designated with a cross) may be used to calculate the direction and translation distance of the relative movement of the fundus camera 10 and the eyeball 20. While the guide information GI is in form of an arrow, the direction and length of the arrow may be used to tell the testee the direction and translation distance of moving the fundus camera 10 or the eyeball 20. It is understood: while the fundus camera 10 includes the distance sensor 113, with the width of the arrow, the processor 110 may indicate the testee to move the fundus camera 10 and the tested eyeball 20 closely to each other or far away from each other. As the fundus does not appear in the sensation image SI of FIG. 6a, the arrow is in a selected color, which is represented by an arrow with slant lines in FIG. 6a.

Referring to FIG. 6b, while the testee who follows the guiding of the guide information makes the image of a portion of the fundus EF appear in the field of vision FV of the sensation image SI, it means that the illumination light L1 provided by the fundus camera 10 may illuminate the funds of the tested eyeball 20. In such a case, the arrow is shown in another selected color like one represented by an arrow filled with black color in FIG. 6b. The direction and the translation distance of the relative movement of the fundus camera 10 and the tested eyeball 20 are acquired by calculating the center of the image of the fundus EF and the center of the sensation image SI. The direction and the length of the arrow are used to tell the testee the direction and the translation distance of the relative movement of the fundus camera 10 and the tested eyeball 20.

Referring to FIG. 6c, while a single-side shadow SH appears in the field of vision FV of the sensation image SI, it means that the illumination light L1 is partially shaded by the rim of the pupil. In the sensation image SI shown in FIG. 6c, the macula MA has appeared in the field of vision FV of the sensation image SI. In such a case, the direction from the center of the shadow SH to the center of the sensation image SI is used as the direction of the arrow; the diameter of the smallest inscribed circle of the shadow SH is used as the length of the arrow, whereby to guide the testee to move the fundus camera 10 or the tested eyeball 20.

The testee continues moving the fundus camera 10 or the tested eyeball 20 according to the guide information GI until the field of vision FV of the sensation image SI is all occupied by the image of the fundus EF, as shown in FIG. 6d. Next, a best shot area BSA is shown in the first display panel 108, and an indicating light is projected onto the best shot area BSA. The indicating light is reflected by the fundus, and the reflected indicating light forms a light spot IL on the sensation image SI. Guided by the guide information GI, the testee moves the light spot IL of the indicating light into the best shot area BSA, which means that the tested eyeball 20 of the testee has been exactly aligned to the fundus camera 10 and that an appropriate distance is maintained therebetween. In such a case, no matter whether the fundus camera 10 automatically shoots the fundus or the testee triggers the fundus camera 10 to shoot the fundus, fundus images with higher quality are obtained, as shown in FIG. 6e. In one embodiment, the light spot IL is generated by an additional light emitting element. In another embodiment, the light spot IL is generated by an intensified infrared illumination light, which is used to search for the fundus originally. The light spot IL favors the testee to align his eyeball to the fundus camera 10. However, the testee may also aligns his eyeball to the fundus camera 10 merely according to the guide information GI. In other words, the indicating light that generates the light spot IL is optional in the present invention.

In one embodiment, the method for self-shooting fundus of the present invention includes steps: providing a fundus camera 10 as shown in FIG. 1; presenting guide information GI on a first display panel 108; the testee who follows the guide information adjusting the relative position of the fundus camera 10 and a tested eyeball 20 to a predetermined position for shooting fundus. In one embodiment, the method for self-shooting fundus of the present invention further includes an optometry method. The structure of the fundus camera 10, the method for guiding the testee to move the fundus camera 10 or the tested eyeball 20, and the optometry method have been described above and will not repeat herein.

Figure 7:
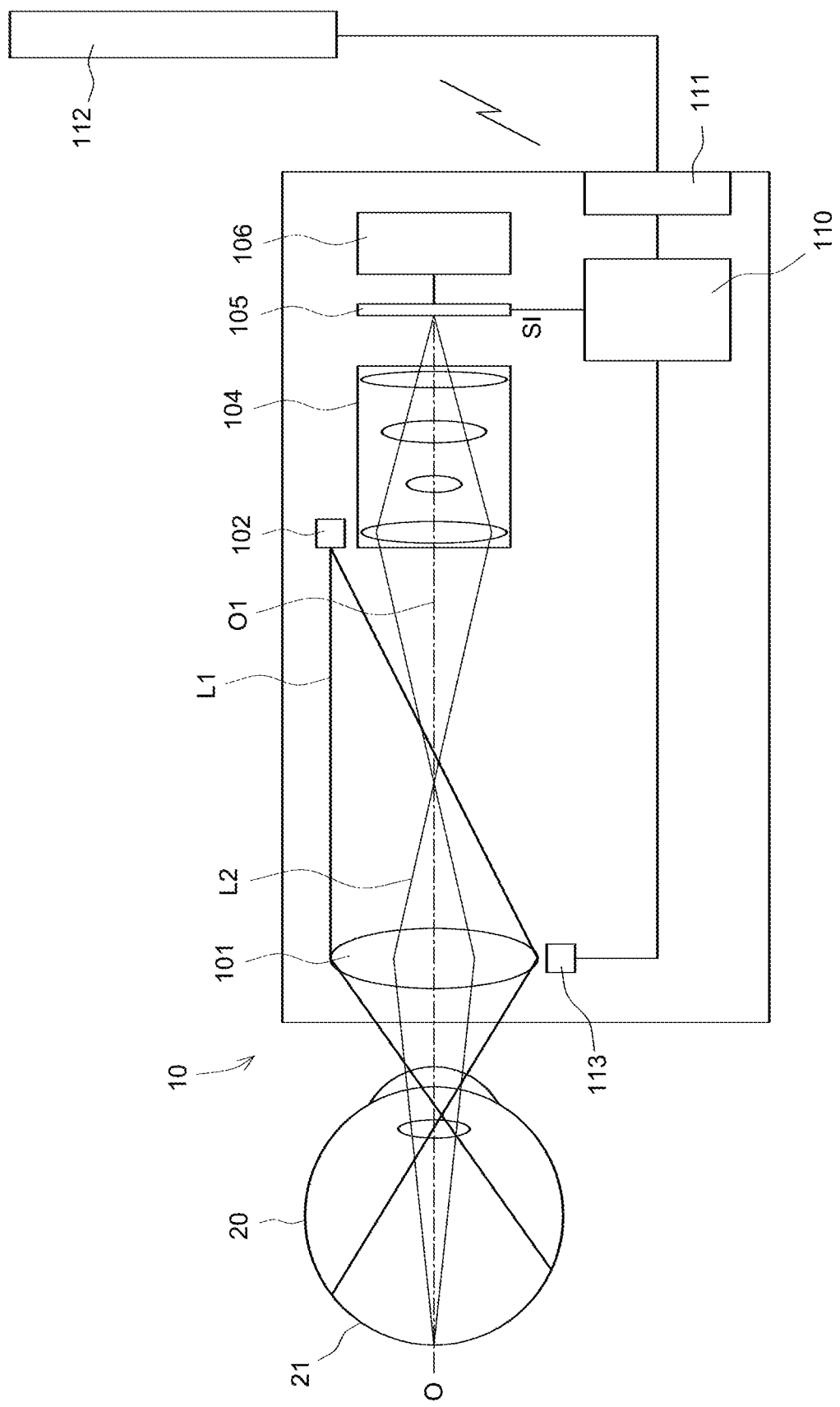
FIG. 7 is a diagram schematically showing a fundus camera according to another embodiment of the present invention.

Refer to FIG. 7 for the fundus camera according to another embodiment of the present invention. In the embodiment shown in FIG. 1, the guide information is presented on the first display panel 108 and imaged on the fundus of the tested eyeball 20 through the third lens group 107, the light splitter 103 and the first lens group 101. In other words, the testee learns the guide information through the tested eyeball 20. In the embodiment shown in FIG. 7, the guide information is presented on the second display panel 112, and the testee uses the untested eyeball to view the second display panel 112 to learn the guide information. In comparison with the fundus camera of the embodiment shown in FIG. 1, the embodiment shown in FIG. 7 may omit the light splitter 103, the third lens group 107 and the first display panel 108.

In conclusion, the present invention proposes a fundus camera and a method for self-shooting fundus, which present guide information on a display panel visible to the testee to guide the testee to adjust the relative position of the fundus camera and the tested eyeball to a predetermined position, whereby the testee can operate the fundus camera by himself to complete the entire photographing process and obtain the fundus images with higher quality. The fundus camera of the present invention can also measure the diopter of the testee to simplify the operation and provide diopter information for the testee.

The foregoing description of specific embodiments reveals the general nature of the inventive subject matter sufficiently so that others can, by applying current knowledge, readily modify and/or adapt it for various applications without departing from the general concept. Therefore, such adaptions and modifications are within the meaning and range of equivalents of the disclosed embodiments. The inventive subject matter embraces all such alternatives, modifications, equivalents, and variations as fall within the spirit and broad scope of the appended claims.

What is claimed is:

1. A fundus camera comprising:
a first lens group having a first side and a second side opposite to the first side, wherein the first side faces a tested eyeball of a testee;
an illumination element disposed on the second side of the first lens group, wherein the first lens group converges an illumination light provided by the illumination element to the tested eyeball;
a second lens group coaxially disposed on the second side of the first lens group, wherein the second lens group comprises at least one lens or one liquid-state lens;
an image sensor disposed on a light output side of the second lens group, wherein an imaging light coming from the tested eyeball is converged by the first lens group and the second lens group to the image sensor to form a sensation image;
a light splitter disposed on the second side of the first lens group, splitting an optical axis of the first lens group into a first sub-optical axis and a second sub-optical axis, wherein the first sub-optical axis is an extension of the optical axis of the first lens group;
a third lens group coaxially disposed on the second sub-optical axis, wherein the third lens group comprises at least one lens or one liquid-state lens;
a first display panel disposed on a light input side of the third lens group, wherein an image light generated by the first display panel is converged by at least the third lens group, the light splitter, and the first lens group in sequence to the tested eyeball;
a first focal length adjuster physically moving a position of the image sensor in the first sub-optical axis or a position of the lens of the second lens group in the first sub-optical axis, or adjusting a curvature of the liquid-state lens of the second lens group, to make the sensation image be imaged on the image sensor;
a processor electrically connected with the image sensor and the first display panel, wherein the processor presents guide information on the first display panel to guide the testee to adjust a relative position of the fundus camera and the tested eyeball to a predetermined position for photography;
a second focal length adjuster physically moving a position of the first display panel on the second sub-optical axis or a position of the lens of the third lens group on the second sub-optical axis, or adjusting a curvature of the liquid-state lens of the third lens group, to make the guide information be imaged on a fundus of the tested eyeball,
wherein the processor electrically connects with the first focal length adjuster and the second focal length adjuster to execute an optometry process by
presenting an optometric pattern on the first display panel,
controlling the second focal length adjuster to adjust a focal length between the first display panel and the third lens group and then controlling the first focal length adjuster to adjust a focal length between the image sensor and the second lens group to obtain a plurality of the sensation images captured by the image sensor, and
analyzing the plurality of sensation images to obtain dioptric information; and
a communication interface electrically connected with the processor, wherein the fundus camera communicates with an external electronic device through the communication interface.

2. The fundus camera according to claim 1, wherein the light splitter is disposed between the first lens group and the second lens group, or disposed between the second lens group and the image sensor.

3. The fundus camera according to claim 1, wherein according to the dioptric information, the processor adjusts a focal length between the first display panel and the third lens group to make an image presented by the first display panel be imaged on the fundus of the testee.

4. The fundus camera according to claim 1 further comprising a second display panel electrically connected with the processor and presenting the sensation image.

5. The fundus camera according to claim 4, wherein the second display panel is a touch control panel able to receive a control instruction input by the testee.

6. The fundus camera according to claim 1 further comprising a distance sensor disposed at an edge of first lens group the and electrically connected with the processor to measure a distance from the fundus camera to the testee.

7. The fundus camera according to claim 6, wherein the guide information includes the distance, a direction from a predetermined shot area to a center of the sensation image, and a translation distance from the predetermined shot area to the center of the sensation image.

8. The fundus camera according to claim 1, wherein the guide information includes a direction from a predetermined shot area to a center of the sensation image, and a translation distance from the predetermined shot area to the center of the sensation image.

9. The fundus camera according to claim 8, wherein the guide information further includes an area indicating the tested eyeball is aligned to the fundus camera between the tested eyeball and the fundus camera.

10. The fundus camera according to claim 1, wherein the first display panel presents a fixation pattern together with the guide information.

11. The fundus camera according to claim 1, wherein the guide information is presented at a fixed position to function as a fixation pattern.

12. The fundus camera according to claim 1, wherein the illumination element is deviated from the optical axis of the first lens group, or the illumination element provides an annular illumination light.

13. The fundus camera according to claim 1, wherein the illumination element includes at least one visible light emitting element and at least one infrared light emitting element.

14. A method for self-shooting fundus, comprising:
providing a fundus camera comprising a first lens group, a second lens group, an illumination element, an image sensor, a light splitter, a third lens group, a first display panel, wherein the first lens group converges an illumination light provided by the illumination element to a tested eyeball of a testee; an imaging light coming from the tested eyeball is converged by the first lens group and the second lens group to the image sensor to form a sensation image; an image light generated by the first display panel is converged by at least the third lens group, the light splitter, and the first lens group to a fundus of the tested eyeball;
presenting guide information on the first display panel; and
according to the guide information, the testee adjusting a relative position of the tested eyeball and the fundus camera to a predetermined position for photography;
presenting an optometric pattern on the first display panel;
controlling a focal length between the first display panel and the third lens group to induce an accommodation relax of the eyeball of the testee;
controlling a focal length of the image sensor and the second lens group to obtain a plurality of sensation images; and
analyzing the plurality of sensation images to obtain dioptric information of the tested eyeball; and
adjusting the focal length between the first display panel and the third lens group according to the dioptric information to make an image presented by the first display panel be imaged on the fundus of the tested eyeball.

15. The method for self-shooting fundus according to claim 14, wherein the guide information includes a direction from a predetermined shot area to a center of the sensation image, and a translation distance from the predetermined shot area to the center of the sensation image.

16. The method for self-shooting fundus according to claim 15, wherein the guide information also includes an area indicating the tested eyeball is aligned to the fundus camera and a distance is maintained between the tested eyeball and the fundus camera.

17. The method for self-shooting fundus according to claim 16, wherein the guide information further includes a distance from the fundus camera to the testee.

18. The method for self-shooting fundus according to claim 14 further comprising presenting a fixation pattern on the first display panel together with the guide information.

19. The method for self-shooting fundus according to claim 14, wherein the guide information is presented at a fixed position to function as a fixation pattern.

* * * * *